(12) United States Patent
Hoerauf

(10) Patent No.: US 8,834,504 B2
(45) Date of Patent: Sep. 16, 2014

(54) LANCET

(75) Inventor: Christian Hoerauf, Oftersheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/344,066

(22) Filed: Jan. 5, 2012

(65) Prior Publication Data

US 2012/0116437 A1 May 10, 2012

Related U.S. Application Data

(63) Continuation of application No. PCT/EP2010/003548, filed on Jun. 12, 2010.

(30) Foreign Application Priority Data

Jul. 10, 2009 (EP) ..................... 09009000

(51) Int. Cl.
*A61B 17/32* (2006.01)
*A61B 5/15* (2006.01)

(52) U.S. Cl.
CPC .................. *A61B 5/1411* (2013.01)
USPC ......................... 606/182; 606/181

(58) Field of Classification Search
USPC ................ 606/167, 170, 181–186, 222, 223; 604/264, 272–274; 600/583; 30/346, 30/346.55, 346.57, 351, 353, 356, 357, 30/278; D24/130, 146, 147
See application file for complete search history.

(56) References Cited

U.S. PATENT DOCUMENTS

| | | | | |
|---|---|---|---|---|
| 2,896,628 A * | 7/1959 | Speelman | ...................... | 606/181 |
| 5,928,207 A * | 7/1999 | Pisano et al. | .................. | 604/272 |
| 7,766,846 B2 * | 8/2010 | Wong et al. | ................... | 600/583 |
| 7,824,382 B2 * | 11/2010 | Reihl et al. | ..................... | 604/272 |
| 7,935,063 B2 * | 5/2011 | Roe | ............................... | 600/584 |

(Continued)

FOREIGN PATENT DOCUMENTS

| | | |
|---|---|---|
| EP | 1 346 686 A2 | 9/2003 |
| EP | 1 709 906 A1 | 10/2006 |

(Continued)

OTHER PUBLICATIONS

International Patent Application PCT/EP2010/003548 International Preliinary Report on Patentability/Written Opinion mailed Jan. 17, 2012.

(Continued)

*Primary Examiner* — David Eastwood
(74) *Attorney, Agent, or Firm* — Woodard, Emhardt, Moriarty, McNett & Henry LLP

(57) ABSTRACT

The invention relates to a lancet having a flat shaft (1) which has an upper side (1*c*) and a lower side (1*b*), the shaft (1) forming at a front end (2) a cutter (1*a*) which ends in a point (2), the cutter (1*a*) having on the underside (1*b*) two cutting edges (4), which run together at the point (2), and the shaft (1) having at least one depression (3) on its underside (1*b*) to receive a sample. The invention provides for the shaft, on its upper side (1*c*), to merge into the cutter (1*a*) at two edges (5) which run together at a vertex (6), and for the upper side (1*c*) of the cutter (1*a*) between the vertex (6) and the front end (2) to be curved convexly, as seen in cross section.

21 Claims, 6 Drawing Sheets

(56) References Cited

U.S. PATENT DOCUMENTS

| | | |
|---|---|---|
| 8,142,366 B2 * | 3/2012 | Haar et al. ............... 600/583 |
| 2002/0168290 A1 * | 11/2002 | Yuzhakov et al. ............ 422/56 |
| 2002/0188310 A1 * | 12/2002 | Seward et al. ............. 606/185 |
| 2003/0078549 A1 * | 4/2003 | Stupar et al. ............. 604/272 |
| 2003/0153939 A1 | 8/2003 | Fritz et al. |
| 2006/0030788 A1 | 2/2006 | Wong et al. |
| 2008/0108910 A1 | 5/2008 | Hein et al. |
| 2008/0262388 A1 | 10/2008 | List et al. |
| 2009/0192409 A1 * | 7/2009 | Wong et al. ............. 600/583 |
| 2009/0240165 A1 * | 9/2009 | Yoneya et al. ............ 600/583 |
| 2009/0287116 A1 | 11/2009 | Konya |

FOREIGN PATENT DOCUMENTS

| | | |
|---|---|---|
| EP | 2 022 399 A1 | 2/2009 |
| RU | 2339306 C2 | 4/2005 |
| WO | 0166010 A1 | 9/2001 |
| WO | 2004041087 A2 | 5/2004 |
| WO | WO 2005/084545 A1 | 9/2005 |
| WO | WO 2008/083844 A1 | 7/2008 |

OTHER PUBLICATIONS

International Patent Application PCT/EP2010/003548 Search Report (Publication WO 2011/003499 A3) mailed Jan. 18, 2011.

* cited by examiner

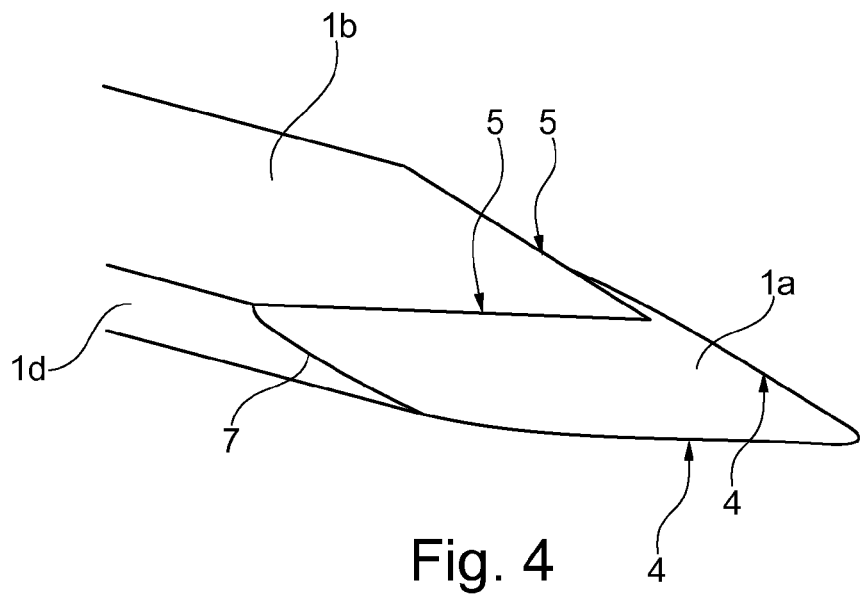
Fig. 4
Fig. 5
Fig. 6
Fig. 7
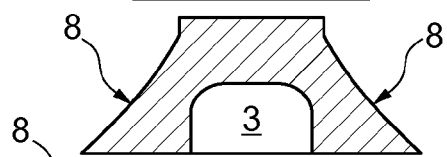
Fig. 8
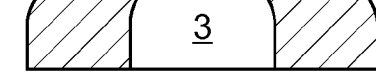
Fig. 9
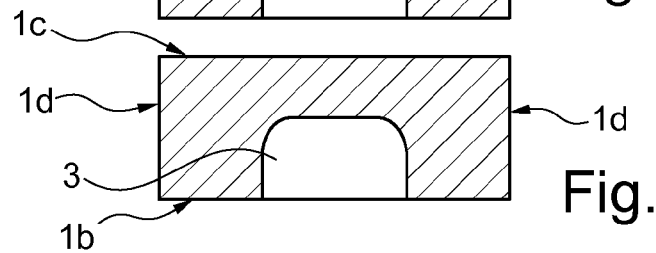
Fig. 10
Fig. 11

LANCET

CROSS-REFERENCE TO RELATED APPLICATIONS

This application is a continuation of International Application No. PCT/EP2010/003548 filed Jun. 12, 2010, which claims the benefit of European Patent Application No. 09009000.2 filed Jul. 10, 2009, which are hereby incorporated by reference.

BACKGROUND

The invention is based on a lancet having the features presented in the preamble of claim 1. Such a lancet is known from WO 2005/084545 A1.

An incessant aim in the development of lancets is to allow taking samples while minimizing pain as far as possible. The object of the present invention is to show a way how this aim can be reached even better.

SUMMARY

This problem is solved by a lancet having the features presented in claim 1. Advantageous refinements of the invention are the subject of subordinate claims.

A lancet according to the invention has a flat shank comprising a top side and a bottom side, these two sides being connected to each other via narrow sides extending in the longitudinal direction of the shank. Such a shank can, for example, be made from sheet metal with low effort and expenditure. At a forward end, the shank of a lancet according to the invention forms a blade which ends in a point. The blade has at its bottom side two cutting edges which converge in the point. On the bottom side, the shank comprises at least one recess for taking a sample. Preferably, this recess is configured as a groove. In the stead or in addition to a groove, recesses having other shapes, for example blind holes, can be arranged on the bottom side of the shank.

In a lancet according to the invention, the blade is delimited on the top side by two edges which converge in a vertex. As seen in cross-section, the top side of the blade is convex between the vertex and the forward end. This means that the blade has a convex top side between the vertex and the forward end, as seen transversely to the longitudinal direction.

The special shape of a blade according to the invention allows puncturing with less pain than this is possible with the lancets known from WO 2005/084545 A1, the blade of which are delimited by plane surfaces and a single upper edge which extends perpendicular to the longitudinal direction of the shank.

The surprisingly advantageous properties of a lancet according to the invention can probably be attributed to the fact that the formation of painful pressure waves can be avoided to the greatest possible extend during a puncture. When a lancet according to the invention penetrates into a patient's body tissue, a puncture channel is produced that is gently expanded to the thickness of the lancet shank by the convex top side of the blade. Since the blade is delimited by two converging edges on the top side and, as seen in cross-section, the top side of the blade is convex between the vertex and the forward end, the puncture channel is, initially, expanded to the full thickness of the lancet shank only over a part of its width. While the lancet penetrates further, the puncture channel is then enlarged to the full thickness of the lancet shank over an increasingly larger part of its width. This is an essential improvement as compared with the lancet known from WO 2005/084545 A1, where the puncture channel, when reaching the full thickness, is also expanded to the full width at the same time.

Since the thickness and width of a lancet are finite, it cannot be avoided that, when a puncture is made, pressure is also exerted on surrounding tissue transversely to the puncture direction. In a lancet according to the invention, this pressure is, advantageously, practically exclusively exerted from the convex top side of the blade and the top side of the shank arranged adjacent thereto. This probably results in that the tissue resting against the bottom side of the shank is compressed to a lesser degree, for which reason body fluid can leak from the tissue resting against the bottom side of the shank particularly easily and can fill the recess which is provided on the bottom side of the shank for the purpose of taking a sample.

An advantageous refinement of the invention provides that the blade is concave along a line extending from the vertex to the forward end. This measure contributes to further reducing the pain connected with the puncture. That is to say that, in this manner, the thickness of the blade, initially, increases only relatively slowly and, subsequently, more rapidly, as seen from the point. Therefore, the thickness of the blade is reduced in a front region. It is assumed that, in the event of a puncture of the lancet, body tissue initially puts up increased resistance which declines while the lancet advances. With a blade having a shape according to the invention, the force a lancet requires to penetrate into body tissues is, advantageously, reduced and, therefore, the pain sensation as well. Preferably, the blade of a lancet according to the invention is concave in longitudinal direction and convex in transverse direction.

Just as is the case with the point, the vertex is, preferably, disposed in the center of the width of the shank. It is, however, also possible that the vertex and/or the point are/is arranged offset from the center, with the result that the two cutting edges or the two upper edges of the blade comprise different lengths. In such a case, the line from the vertex to the forward end does not extend exactly in the longitudinal direction of the shank but at a slightly slanted angle in relation thereto.

A further advantageous refinement of the invention provides that the upper edges of the blade extend further to the rear than the cutting edges. In this manner, the pain connected with a puncture can be further reduced. Therein, the blade is, preferably, delimited by lateral edges which connect the rear end of a cutting edge to the rear end of one of the upper edges. Preferably, the lateral edges enclose an acute angle with a bottom edge of the shank that extends behind the blade, wherein said angle can, for example, range from 10° to 60°, particularly from 15° to 35°.

A further advantageous refinement of the invention provides that the recess provided for taking a sample is configured as a groove. Preferably, this groove ends at a distance from the forward end of the shank, particularly between the vertex and the forward end of the shank. Most preferably, the groove has a section which is arranged between the cutting edges and in which the cross-sectional area of the groove decreases towards the forward end. The cross-sectional area of the groove can decrease in the area of the blade by a reduction in the width or the depth of the groove, preferably in both the width and the depth. Preferably, the cross-sectional area, i.e., the width and/or the depth, decreases along a length that is in excess of the maximum width of the groove. In this manner, the groove can come up nearer to the forward end of the blade without the mechanical stability of the blade being impaired.

At the end of the groove, the thickness of the blade is, preferably, less than two thirds, preferentially, no more than half the thickness of the shank. At the end of the groove, the width of the blade is, most preferably, less than two thirds, preferentially, no more than half the width of the shank. Behind the blade, the depth of the groove is, preferably, more than half the thickness of the shank.

Usually a fluid transport by means of capillary forces requires that the capillary cross-section does not increase because penetration of a fluid into an increasing capillary means that the boundary surface between fluid and air increases and is, therefore, unfavorable from an energetic point of view. For this reason, it could be assumed that a tapering section of the groove is not able to contribute to taking a sample. Surprisingly, however, this is not the case. When the groove has a cross-sectional area that decreases towards the end of the blade, the puncture depth required for taking a sample can be reduced. For this reason, taking a sample with a lancet according to the invention is, advantageously, connected with less pain.

Therefore, the aspect of the invention that provides a groove on the bottom side of the lancet, the cross-sectional area of which decreases towards the forward end, also has an independent importance. For this reason, the present invention also relates to a lancet with a flat shank which has a top side and a bottom side wherein, at a forward end, the shank forms a blade which ends in a point, the blade comprises two cutting edges on the bottom side, said cutting edges converging in the point, and the shank comprises at least one groove for taking a sample on its bottom side, wherein the groove comprises a section arranged between the cutting edges, the cross-sectional area of the groove decreasing towards the forward end in said section. Preferably, the cross-sectional area decreases along a length which is in excess of the width of the groove, more preferably in excess of the thickness of the shank, particularly in excess of the width of the shank.

A lancet according to the invention having a groove for taking a sample that is arranged on the bottom side of the shank is also to particular advantage in that the danger of an obstruction of the groove or an impairment of a hydrophilic coating contained in the groove is reduced.

Preferably, a lancet according to the invention is produced from metal, preferably from steel. Therein, use is made of a strip of sheet metal for the shank of the lancet. The blade and one or a plurality of recesses for taking a sample can be formed by etching, preferably by wet chemical etching. To achieve this, a strip of sheet metal can be coated with photoresist on all sides. By exposing and, subsequently, washing off the photoresist in an appropriate manner, the latter can be removed from the bottom side at those points where it is intended to form the at least one recess for taking a sample. On the top side, the photoresist can be removed in the complete region in front of two V-shaped lines which will, subsequently, form the upper edges of the blade. In addition, the photoresist can be removed at the narrow sides in the region in front of a line that extends from top to bottom and, subsequently, forms a lateral delimiting edge of the blade. By the subsequent action of an etching agent, the shape of the blade according to the invention can be produced. As an alternative, however, a lancet according to the invention can, for example, be produced by means of laser beam cutting.

Advantageously, a lancet according to the invention allows taking a sample from beneath the skin. The danger of a contamination on the skin surface can, therefore, be avoided. This is to important advantage, particularly in the determination of the glucose concentration, because sugar is often found on the skin, for example after the consumption of sweet desserts. To be able to take a subcutaneous sample, advantageous use can be made of puncturing devices with which the return movement of the lancet is made more slowly than the advance movement. Devices with suitable puncturing drives are described in EP 1 709 906 A1 and US 2008/0262388 A1.

One aspect of the present invention, therefore, relates to a puncturing system with a lancet according to the invention and a puncturing device which, on puncturing, causes an advance movement of the lancet and a subsequent return movement wherein the return movement takes place at a lower speed than the advance movement. In a first section of the return movement, the lancet is, preferably, withdrawn at a faster speed than in a subsequent second section. In this manner, the lancet only remains in pain-sensitive body tissue for as short a time as possible, however, stays in pain-insensitive body tissue, for example, the stratum corneum layer of the epidermis, for a prolonged period of time for sample taking purposes.

A lancet according to the invention can be formed such that, in the event of a puncture through body tissue, its blade is deflected transversely to the puncture direction and bent towards its bottom side. During the return movement, a cavity will then form between the bottom side of the blade and the tissue, said cavity being quickly filled with body fluid. During the slow return movement or during the slow section of the return movement, the recess arranged on the bottom side of the lancet can, advantageously, receive a sample. The formation of a cavity between the bottom side of the blade and surrounding body tissue can also be caused or promoted by a shift in or compression of tissue occurring during the puncture.

For this reason, a lancet that is bent during the puncture and comprises a recess for taking a sample on its bottom side allows taking a sample in an improved manner. One aspect of the invention, which may also have an independent importance, therefore relates to a lancet with a flat shank which has a top side and a bottom side wherein, at a forward end, the shank forms a blade which ends in a point, the blade comprises two cutting edges on the bottom side, said cutting edges converging in the point, and the shank comprises at least one recess for taking a sample on its bottom side, wherein the shank comprises a bending stiffness of less than 0.1 kNmm$^2$ (kilonewton multiplied by square millimeters), preferably less than 0.05 kNmm$^2$, more preferably 0.03 to 0.001 kNmm$^2$.

The bending stiffness is the product from the modulus of elasticity of the material and the second moment of area of the lancet shank. In a shank with a rectangular cross-section, the second moment of area is $I=a^3b/12$ where a is the shank thickness and b is the shank width. In a flat lancet with a rectangular cross-section, the second moment of area and, therefore, the bending stiffness is somewhat reduced because of the groove.

Preferably, the shank is made of metal, more preferably of steel. As an alternative, however, use can also be made of plastic. Preferably, the shank has a width of less than 0.5 mm, for example between 0.2 mm and 0.4 mm. Preferably, the thickness of the shank is no more than 0.3 mm, more preferably between 0.2 mm and 0.05 mm, most preferably between 0.20 mm and 0.08 mm.

BRIEF DESCRIPTION OF THE DRAWINGS

Further details and advantages of the invention are illustrated by means of exemplary embodiments with reference being made to the enclosed drawings. Therein, equal and corresponding parts are designated with consistent reference symbols. In the drawings.

FIG. 4 is an inclined view of the lancet;

FIG. 5 is a cross-sectional view taken from intersection line AA of FIG. 3;

FIG. 6 is a cross-sectional view taken from intersection line BB of FIG. 3;

FIG. 7 is a cross-sectional view taken from intersection line CC of FIG. 3;

FIG. 8 is a cross-sectional view taken from intersection line DD of FIG. 3;

FIG. 9 is a cross-sectional view taken from intersection line EE of FIG. 3;

FIG. 10 is a cross-sectional view taken from intersection line FF of FIG. 3;

FIG. 11 is a cross-sectional view taken from intersection line GG of FIG. 3;

DETAILED DESCRIPTION

Figure 1:
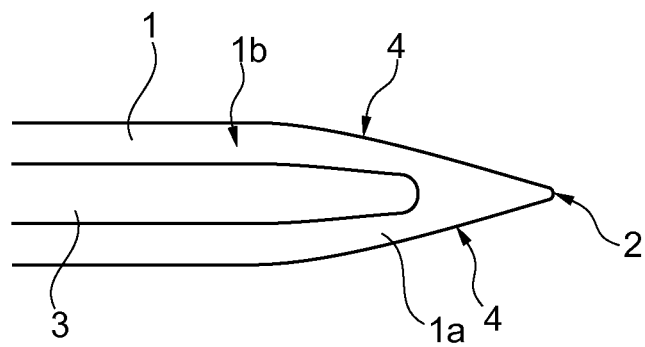
FIG. 1 is a bottom view of an exemplary embodiment of a lancet according to the invention.
Figure 2:
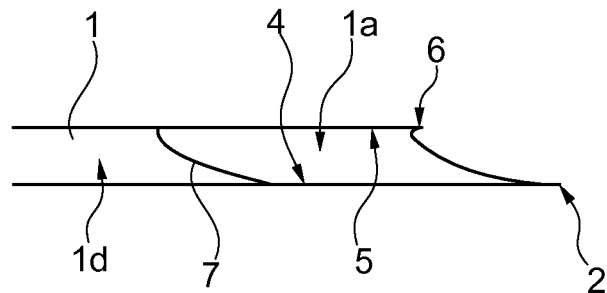
FIG. 2 is a lateral view of FIG. 1.
Figure 3:
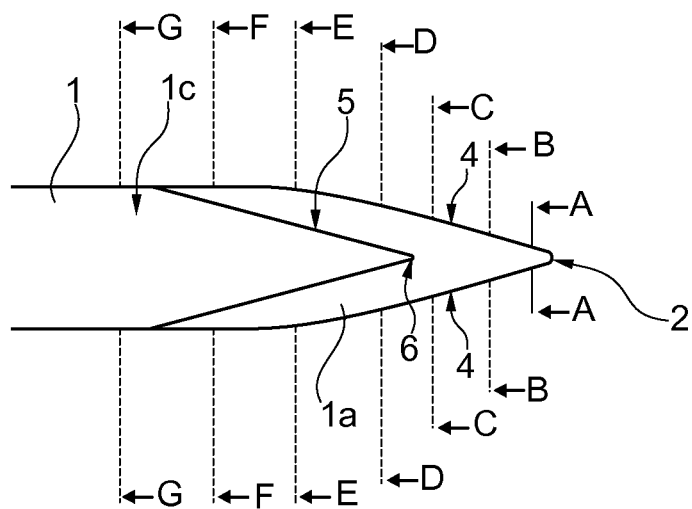
FIG. 3 is a top view of the lancet shown in FIG. 1.

The lancet that is shown schematically in FIGS. 1 to 11 has a flat shank 1 which, at its forward end, forms a blade 1a which ends in a point 2. The shank 1 has a bottom side 1b that is shown in FIG. 1 and a top side 1c that is shown in FIG. 3. The bottom side 1b and the top side 1c are connected to each other via narrow sides 1d extending in the longitudinal direction of the shank 1.

On its bottom side 1b, the shank 1 comprises a recess 3 for taking a sample. Preferably, this recess 3 is configured as a groove. It is, however, also possible to use a plurality of recesses which are, for example, arranged as tapped blind holes on the bottom side 1b.

The blade 1a has two lower edges which converge in the point 2. These lower edges are configured as cutting edges 4. In the exemplary embodiment shown, the cutting edges 4 converge in a wedgelike manner and enclose an acute angle. Preferably, the cutting edges 4 enclose an angle of less than 60°, preferably of less than 45°, more preferably an angle of less than 40°. Preferably, the angle enclosed between the two cutting edges 4 is at least 20°, more preferably at least 25°.

In addition to the two cutting edges 4, the blade 1a has two upper edges 5 which converge in a vertex 6. On the top side 1c, the blade 1a is, therefore, delimited by the two upper edges 5 that converge in a wedgelike manner and, on the bottom side 1b, by the cutting edges 4 that converge in a wedgelike manner. In the exemplary embodiment shown, the upper edges 5 and the cutting edges 4 extend in parallel but can also enclose different angles. Preferably, the upper edges 5 enclose an acute angle. In the exemplary embodiment shown, this angle is less than 60°, for example, 10° to 50°, particularly 20° to 45°.

Preferably, the vertex 6 is arranged behind the point 2 by more than the thickness of the shank 1. Therefore, the component of the distance between the vertex 6 and the point 2, i.e., the forward end point of the lancet, said component being measured in the longitudinal direction of the shank 1, preferably is more than the thickness of the shank 1. As is the case with the exemplary embodiment shown, the vertex 6 is, preferably, arranged behind the point 2 by more than twice the thickness of the shank 1. Preferably, the width of the shank 1 is two to three times its thickness.

The upper edges 5 extend further to the rear than the cutting edges 4. On each of its sides, the blade 1a is laterally delimited by an edge 7 which connects the rear end of a cutting edge 4 to the rear edge of an upper edge 5. Preferably, the edge 7 encloses an acute angle with the lower edge of the narrow side 1d arranged on its side, for example an angle between 10° and 60°, more particularly between 15° and 35°. The edge 7 can enclose an obtuse angle with the cutting edge 4 arranged on its side.

Therein, FIG. 2 shows that the blade 1a is concave along a line extending from the vertex 6 to the forward end 2. The top side 1b has an undercut at the vertex 6.

FIGS. 5 to 11 show a series of cross-sections of the lancet along the intersection lines shown in FIG. 3. Therein, FIG. 5 is a sectional view taken from intersection line AA, FIG. 6 taken from intersection line BB, FIG. 7 taken from intersection line CC, FIG. 8 taken from intersection line DD, FIG. 9 taken from intersection line EE, FIG. 10 taken from intersection line FF, and FIG. 11 taken from intersection line GG.

FIGS. 5 to 7 show that the top side of the blade 1a is convex between the vertex 6 and the forward end point 2, as seen in cross-section. Therein, FIGS. 5 to 7 also show that the cutting edges 4 comprise a cutting angle that decreases towards the forward end 2. Therein, the cutting angle decreases continuously towards the forward end 2. As a result, the puncture channel produced in a patient's body tissue in the event of a lancet puncture becomes thicker or wider in a continuous manner, this being advantageous for a puncture with reduced pain.

FIGS. 8 to 10 show that the blade 1a has concave lateral surfaces 8 behind the vertex 6, particularly between the vertex 6 and the rear end of the cutting edges 4.

The bottom side 1b of the shank 1 is plane or concave. Therein, FIGS. 5 to 11 show that the bottom side 1b of the shank 1, particularly the bottom side of the blade 1a, is plane in a marginal region on either side. Exclusive of the recess 3 for taking a sample, the complete bottom side 1b of the shank 1 is plane. As a result of the recess 3, the bottom side 1b of the shank 1 is concave in the corresponding region.

In a lancet according to the invention, the bottom side 1b between the forward end 2 and the vertex 6 or even the complete bottom side of the blade 1a can be free from recesses 3 for taking a sample. Preferably, however, the recess 3 also extends in the region of the blade 1a. In order to minimize the puncture depth required for obtaining a sample, it is usually advantageous if the recess 3 extends on the bottom side 1b into the region between the vertex 6 and the forward end 2. In order to not impair the mechanical stability of the blade 1a, it is, in general, advantageous if the groove 3 ends at a distance from the forward end 2. Such a groove 3 that is arranged on the bottom side 1b of the shank is to advantage in that it is not obstructed by the material of a sterile protective foil when the latter is punctured.

In the exemplary embodiment shown, the groove 3 extends beyond the vertex 6. Therein, FIG. 1 shows that the groove 3 continuously tapers in a section in the region of the blade 1*a*. Therein, the length of the tapering section is in excess of the maximum width of the groove 3. In the complete tapering section, the depth of the groove 3 continuously decreases towards the forward end. In other words, the cross-sectional area of the groove 3 decreases in the section arranged between the cutting edges 4.

Preferably, the maximum width of the groove 3, i.e., the groove width behind the blade 1*a*, is less than half the shank width. Preferably, the maximum depth of the groove, i.e., the groove depth behind the blade 1*a*, is in excess of half the shank thickness. The shank thickness should be less than 0.3 mm and, preferably, is between 80 μm and 200 μm, more preferably between 80 μm and 180 μm. For example, the shank width can be between 0.2 mm and 0.5 mm, preferably 250 μm to 400 μm.

The preferred material is steel, particularly stainless steel. The bending stiffness of the lancet shank should not exceed 0.1 kNmm$^2$, preferably be less than 0.05 kNmm$^2$, more preferably less than 0.02 kNmm$^2$. Advantageous values range, in particular, from 0.01 to 0.001 kNmm$^2$.

Lancets with such a low bending stiffness are elastically bent when puncturing body tissue. Therein, the bottom side of the lancet that comprises the groove 3 is the inner surface of the bend, with the result that, when the lancet is withdrawn, a cavity is formed on the bottom side and, therefore, in the vicinity of the groove 3, said cavity being filled with body fluid. For this reason, taking a sample is improved by the bending of the lancet.

Figure 12:
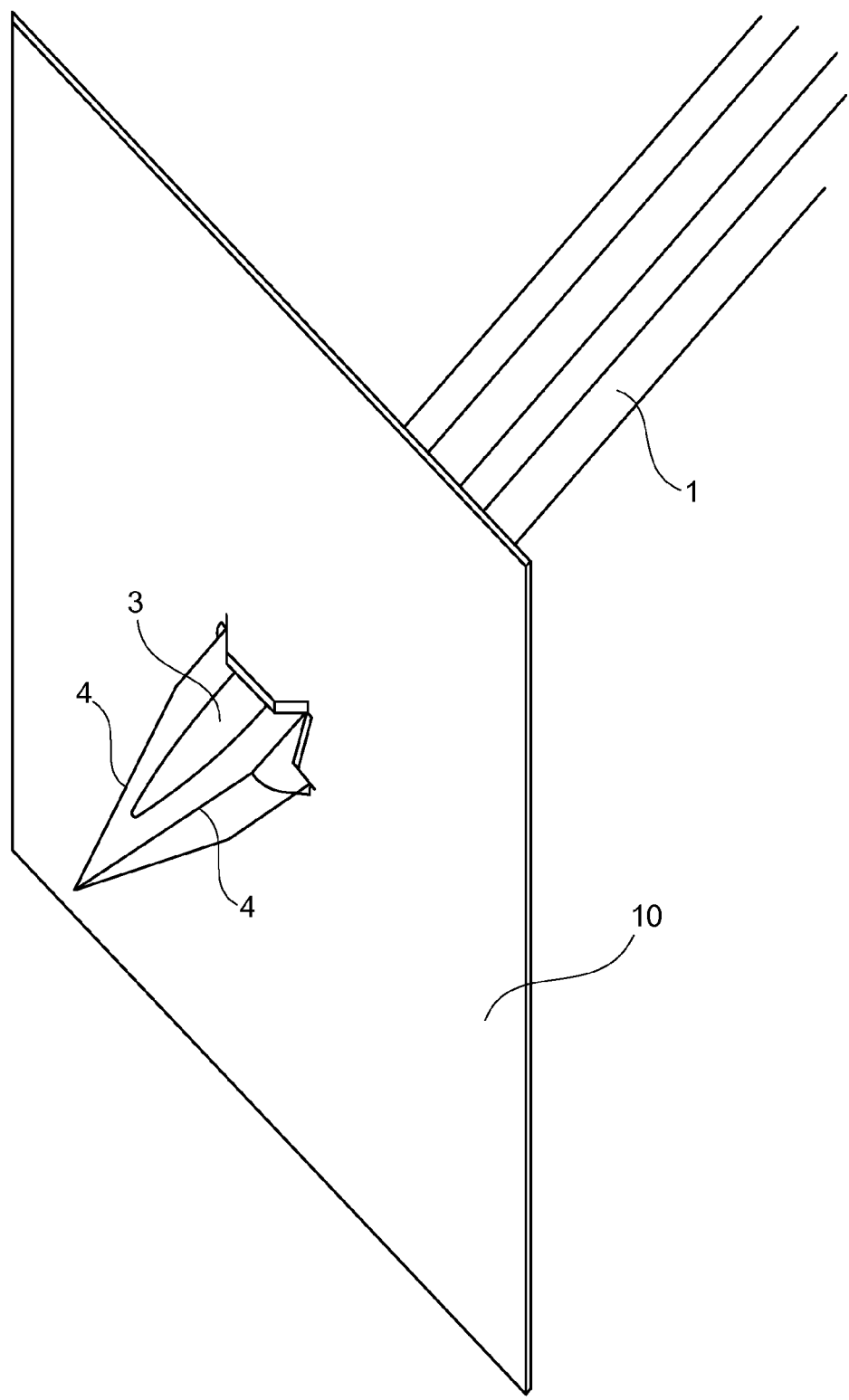
FIG. 12 shows an exemplary embodiment of a lancet according to the invention while puncturing a sterile protective foil.

FIG. 12 shows an exemplary embodiment of a lancet according to the invention while a sterile protective foil 10 is punctured. The sterile protective foil 10 can, for example, be a metal foil, particularly an aluminum foil, a plastic foil or a metal foil coated with plastic or a metal-coated plastic foil. For example, a chamber of a lancet magazine can be closed with such a sterile protective foil 10, in order to protect a lancet arranged therein against harmful environmental influences. Since, in a lancet according to the invention, the groove 3 for taking a sample is arranged on the bottom side of the shank, the groove 3 is not impaired when the sterile protective foil 10 is punctured. That is to say that the cutting edges 4 of the lancet cause the sterile protective foil 10 to be cut open on the bottom side of the lancet in parallel to the bottom side of the shank, with the result that the formation of foil residues which might obstruct the groove 3 are counteracted. It is also to advantage that parts of the punctured sterile protective foil 10 are prevented from projecting into the interior region of the groove 3 during puncturing and, by sliding along a surface of the groove 3, from impairing a hydrophilic coating that, preferably, exists there.

Figure 13:
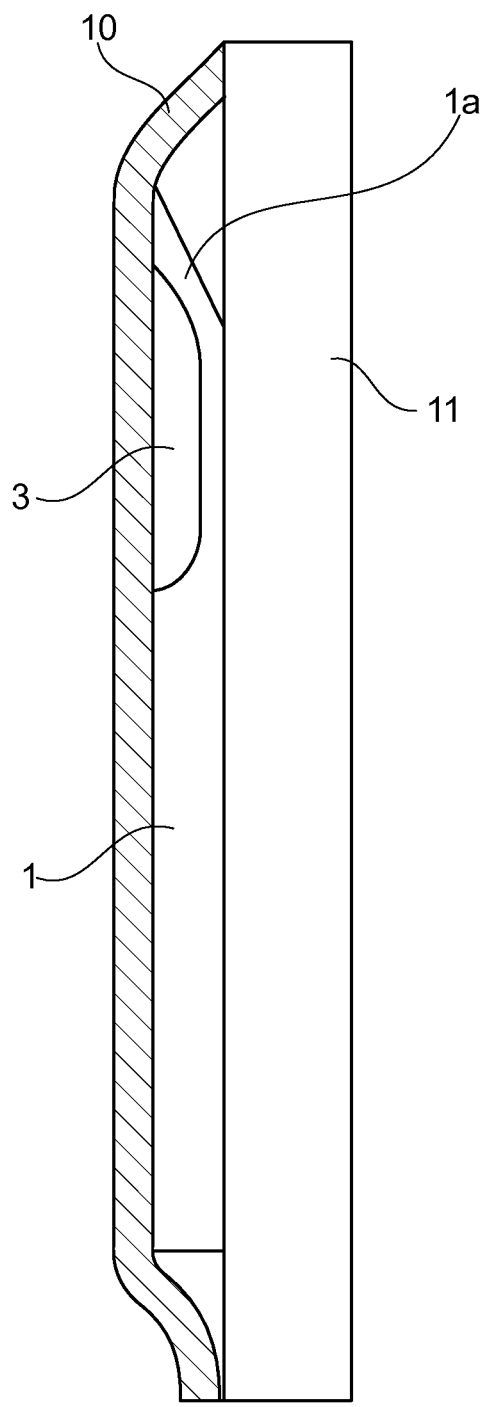
FIG. 13 shows an exemplary embodiment of a lancet according to the invention on a carrier tape.

Instead of arranging a lancet according to the invention in a magazine chamber closed with a sterile protective foil 10, it is also possible to arrange lancets according to the invention on a carrier tape side by side, as this is, for example, known from WO 2008/083844 A1. Preferably, a lancet according to the invention is arranged on a carrier tape with its top side while its bottom side is covered by a sterile protective foil. FIG. 13 is a sectional view of an appropriate exemplary embodiment with a carrier tape 11, a lancet and a sterile protective foil 10.

The sterile protective foil 10 is thinner than the carrier tape 11, preferably no more than half the latter's thickness. The sterile protective foil 10 rests loosely on the lancet and is connected to the carrier tape 11 in a substance-to-substance bonded manner, for example glued or welded. The lancet shank 1 can be glued to the carrier tape 11 in a rear region that is remote from the blade 1*a*. In a front region, the lancet shank 1, preferably, rests loosely on the carrier tape 11, with the result that, in order to make a puncture, the blade 1*a* can be freed from the sterile protective foil by bending the carrier tape 11, as this is described in WO 2008/083844 A1.

Figure 14:
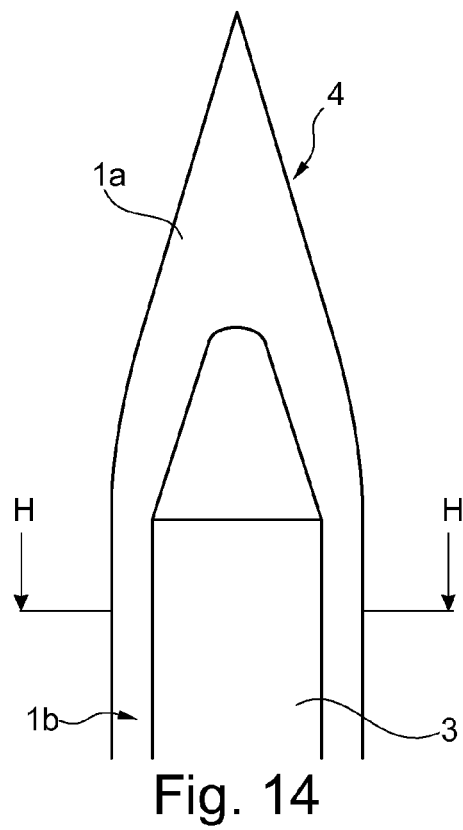
FIG. 14 shows a further exemplary embodiment of a lancet according to the invention.
Figure 15:
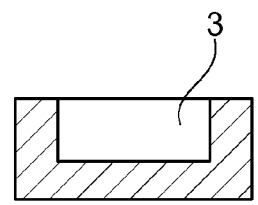
FIG. 15 is a sectional view of FIG. 14.

FIG. 14 shows a further exemplary embodiment of a lancet and FIG. 15 is a related sectional view taken from intersection line HH. This lancet differs from the lancet shown in FIGS. 1 to 11 in that the recess 3 for taking a sample is configured as a groove that is somewhat wider. This allows taking increased sample volumes.

Figure 16:
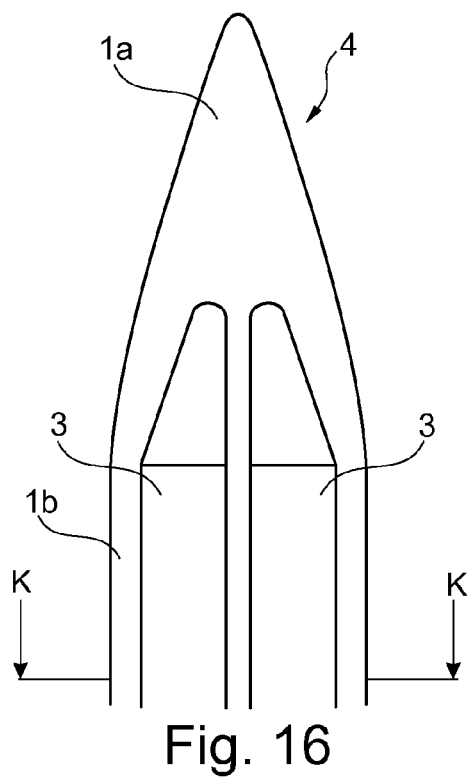
FIG. 16 shows a further exemplary embodiment of a lancet according to the invention.
Figure 17:
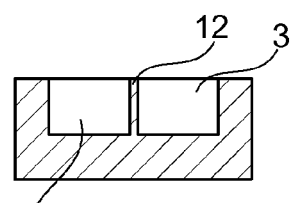
FIG. 17 is a sectional view of FIG. 16.

FIG. 16 shows a further exemplary embodiment of a lancet and FIG. 17 is a related sectional view taken from intersection line KK. This lancet differs from the exemplary embodiment of FIGS. 14 and 15 in that, instead of a single recess 3 configured as groove, there are two recesses 3 that extend in parallel and are configured as groove. The dividing wall 12 between the two recesses 3 reduces the total volume of the two recesses 3 only to an insignificant degree, however, results in significantly increased capillary forces. For this reason, the two recesses 3 of the exemplary embodiment shown in FIG. 16 are filled with body fluid at a higher speed than the single recess of the exemplary embodiment shown in FIGS. 14 and 15.

Figure 18:
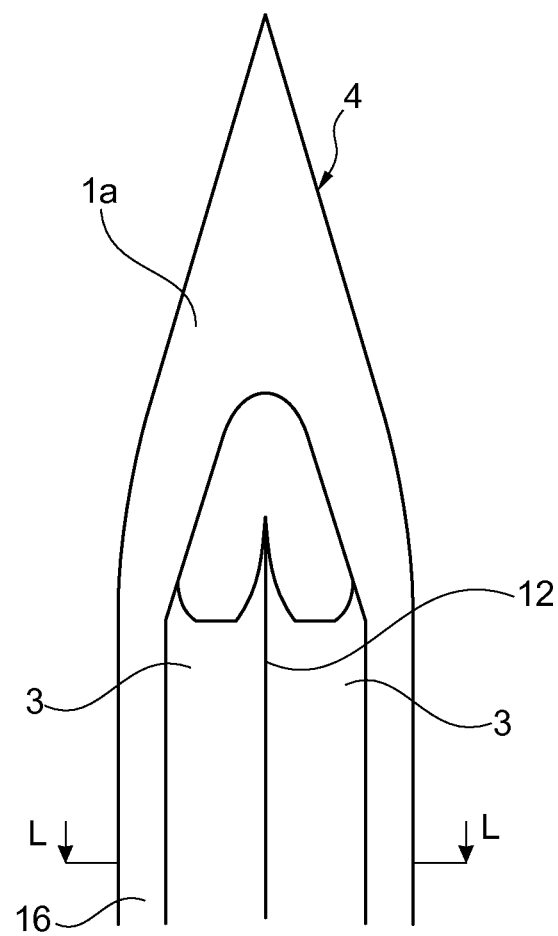
FIG. 18 shows a further exemplary embodiment of a lancet according to the invention.
Figure 19:
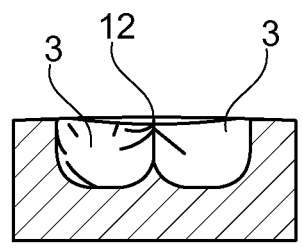
FIG. 19 shows a sectional view of FIG. 18.

FIG. 18 shows a further exemplary embodiment of a lancet and FIG. 19 is a related sectional view taken from intersection line LL. This lancet differs from the exemplary embodiment of FIG. 18 only in that the dividing wall 12 between the two recesses 3 is reduced. For this reason, the two recesses 3 are connected on the surface but are subdivided into two parallel channels in the interior region by means of the dividing wall 12. The dividing wall 12 also causes an increase in the capillary forces and, therefore, a faster filling of the recess 3.

LIST OF REFERENCE NUMERALS 1 shank
1*a* blade
1*b* bottom side
1*c* top side
1*d* narrow side
2 point
3 recess
4 cutting edges
5 upper edges
6 vertex
7 edge
8 lateral surface
10 sterile protective foil
11 carrier tape
12 dividing wall

The invention claimed is:

1. A lancet comprising a flat shank having a top side and a bottom side, the shank forming a blade at a forward end, the blade terminating in a point, the blade having two cutting edges at the bottom side, the cutting edges converging in the point, and the shank having on its bottom side at least one recess for receiving a sample, characterized in that the shank turns into the blade on its top side at two edges which converge in a vertex, and that the top side of the blade is curved convexly between the vertex and the forward end, as seen in cross-section.

2. The lancet according to claim 1, characterized in that the blade is formed concavely along a line running from the vertex to the forward end.

3. The lancet according to claim 1, characterized in that the top side has an undercut at the vertex.

4. The lancet according to claim 1, characterized in that the blade has concave lateral surfaces between the vertex and the rear end of the cutting edges.

5. The lancet according to claim 1, characterized in that both edges, which delimit the blade on the top side, run parallel to the cutting edges.

6. The lancet according to claim 1, characterized in that the vertex is arranged behind the point by more than the thickness of the shank.

7. The lancet according to claim 1, characterized in that the two edges, which delimited the blade on the top side, enclose an acute angle.

8. The lancet according to claim 1, characterized in that the cutting edges have a cutting angle that decreases towards the forward end.

9. The lancet according to claim 1, characterized in that the bottom side of the blade is plane at least in a marginal region along the cutting edges.

10. The lancet according to claim 1, characterized in that the bottom side of the shank is plane exclusive of the recess for receiving a sample.

11. The lancet according to claim 1, characterized in that the upper edges extend further back than the cutting edges.

12. The lancet according to claim 1, characterized in that the recess is a groove which extends beyond the vertex and has a section arranged between the cutting edges, in said section the area of a cross-section of the groove decreases towards the forward end.

13. The lancet according to claim 1, characterized in that the shank has a bending stiffness of less than $0.1$ $kNmm^2$.

14. A puncturing system comprising a lancet according to claim 1 and a puncturing device that, during a puncture, causes a forward motion of the lancet and subsequently a retracting motion, wherein the retracting motion is slower than the forward motion.

15. The lancet according to claim 13, wherein the bending stiffness of the shank is less than $0.05$ $kNmm^2$.

16. The lancet according to claim 13, wherein the bending stiffness of the shank is less than $0.03$ to $0.01$ $kNmm^2$.

17. The lancet according to claim 1, wherein the at least one recess includes two grooves extending parallel to one another for receiving the sample.

18. The lancet according to claim 17, wherein the groove has a section arranged between the cutting edges, wherein the area of cross-section of the groove decreases in that section towards the forward end.

19. A lancet comprising a flat shank having a top side and a bottom side,
the shank forming a blade at a forward end, the blade terminating in a point,
the blade having cutting edges on the bottom side, the cutting edges converging in the point, and
the shank having on the bottom side at least one groove for receiving a sample, characterized in that
the groove has a section arranged between the cutting edges,
wherein the area of cross-section of the groove decreases in that section towards the forward end, wherein the groove has a depth, wherein the depth of the groove decreases towards the forward end, wherein the shank turns into the blade on its top side at two edges which converge in a vertex and the groove extends beyond the vertex.

20. The lancet according to claim 19, wherein the at least one groove includes two grooves extending parallel to one another for receiving the sample.

21. The lancet according to claim 19, wherein the thickness of the blade is less than two thirds of the thickness of the shank at the forward end of the groove.

\* \* \* \* \*